(12) United States Patent
Zhang et al.

(10) Patent No.: US 6,214,813 B1
(45) Date of Patent: Apr. 10, 2001

(54) PYRAZOLE COMPOUNDS

(75) Inventors: Zaihui Zhang, Richmond; Jun Yan; Danny Leung, both of Coquitlam; Penelope C. Costello, Vancouver; Jasbinder Sanghera, Richmond, all of (CA)

(73) Assignee: Kinetek Pharmaceuticals, Inc., Vancouver (CA)

( * ) Notice: Subject to any disclaimer, the term of this patent is extended or adjusted under 35 U.S.C. 154(b) by 0 days.

(21) Appl. No.: 09/544,908

(22) Filed: Apr. 7, 2000

(51) Int. Cl.[7] .................. A61K 31/415; A61K 31/655
(52) U.S. Cl. .................. 514/150; 514/151; 514/404; 514/406
(58) Field of Search .................. 514/150, 151, 514/404, 406

(56) References Cited

PUBLICATIONS

Dubenko et al., Chemical Abstracts, 64:5068f, 1966.*
Kitaev et al., Chemical Abstracts, 82:66061, 1975.*
Studennikova et al., Chemical Abstracts, 105:191071, 1986.*
Delcommenne et al. (Sep. 1998), "Phosphoinositide–3–OH Kinase–Dependent Regulation of Glycogen Synthase Kinase 3 and Protein Kinase B/AKT by the Integrin–Linked Kinase," *Proc. Natl. Acad. Sci. USA*, vol. 95:11211–6.

Kandeel et al. (1985), "Activated Nitriles in Heterocyclic Synthesis: Reaction of Cyanogen Bromide with some Functionality Substituted Enamines," *J. Chem. Sok. Perkin. Trans.*, pp. 1499–1501.

* cited by examiner

*Primary Examiner*—Fiona T. Powers
(74) *Attorney, Agent, or Firm*—Bozicevic, Field & Francis LLP; Pamela J. Sherwood

(57) ABSTRACT

Pharmaceutical compositions and compounds are provided. The compounds of the invention have anti-proliferative activity, and may promote apoptosis in cells lacking normal regulation of cell cycle and death. In one embodiment of the invention, formulations of the compounds in combination with a physiologically acceptable carrier are provided. The pharmaceutical formulations are useful in the treatment of hyperproliferative disorders, which disorders include tumor growth, lymphoproliferative diseases, angiogenesis. The compounds of the invention are substituted pyrazoles and pyrazolines.

18 Claims, No Drawings

PYRAZOLE COMPOUNDS

BACKGROUND OF THE INVENTION

It has become increasingly clear in recent years that cell death is as important to the health of a multicellular organism as cell division: where proliferation exists, so must a means of regulating its cellular progeny. By repeated cell division and differentiation throughout development or tissue repair, surplus or even harmful cells are generated, and they must be removed or killed. In adults, senescent cells are removed and replaced by newly generated cells to maintain homeostasis.

The delicate interplay between growth and cell death in an organism is mirrored in the complex molecular balance that determines whether an individual cell undergoes division; arrests in the cell cycle; or commits to programmed cell death. Signal transduction is the term describing the process of conversion of extracellular signals, such as hormones, growth factors, neurotransmitters, cytokines, and others, to a specific intracellular response such as gene expression, cell division, or apoptosis. This process begins at the cell membrane where an external stimulus initiates a cascade of enzymatic reactions inside the cell that typically include phosphorylation of proteins as mediators of downstream processes which most often end in an event in the cell nucleus. The checks and balances of these signal transduction pathways can be thought of as overlapping networks of interacting molecules that control "go-no go" control points. Since almost all known diseases exhibit dysfunctional aspects in these networks, there has been a great deal of enthusiasm for research that provides targets and therapeutic agents based on signal transduction components linked to disease.

Dysregulation of cell proliferation, or a lack of appropriate cell death, has wide ranging clinical implications. A number of diseases associated with such dysregulation involve hyperproliferation, inflammation, tissue remodelling and repair. Familiar indications in this category include cancers, restenosis, neointimal hyperplasia, angiogenesis, endometriosis, lymphoproliferative disorders, graft-rejection, polyposis, loss of neural function in the case of tissue remodelling, and the like. Such cells may lose the normal regulatory control of cell division, and may also fail to undergo appropriate cell death.

In one example, epithelial cells, endothelial cells, muscle cells, and others undergo apoptosis when they lose contact with extracellular matrix, or bind through an inappropriate integrin. This phenomenon, which has been termed "anoikis" (the Greek word for "homelessness"), prevents shed epithelial cells from colonizing elsewhere, thus protecting against neoplasia, endometriosis, and the like. It is also an important mechanism in the initial cavitation step of embryonic development, in mammary gland involution, and has been exploited to prevent tumor angiogenesis. Epithelial cells may become resistant to anoikis through overactivation of integrin signaling. Anoikis resistance can also arise from the loss of apoptotic signaling, for example, by overexpression of Bcl-2 or inhibition of caspase activity.

An aspect of hyperproliferation that is often linked to tumor growth is angiogenesis. The growth of new blood vessels is essential for the later stages of solid tumor growth. Angiogenesis is caused by the migration and proliferation of the endothelial cells that form blood vessels.

In another example, a major group of systemic autoimmune diseases is associated with abnormal lymphoproliferation, as a result of defects in the termination of lymphocyte activation and growth. Often such diseases are associated with inflammation, for example with rheumatoid arthritis, insulin dependent diabetes mellitus, multiple sclerosis, systemic lupus erythematosus, and the like. Recent progress has been made in understanding the causes and consequences of these abnormalities. At the molecular level, multiple defects may occur, which result in a failure to set up a functional apoptotic machinery.

The development of compounds that inhibit hyperproliferative diseases, particularly where undesirable cells are selectively targeted, is of great medical and commercial interest.

Relevant literature:

The regulation of integrin linked kinase by phosphatidylinositol (3,4,5) trisphosphate is described by Delcommenne et al. (1998) *Proc Natl Acad Sci* 95:11211–6. Activated nitrites in heterocyclic synthesis are discussed in Kandeel et al. (1985) *J. Chem. Soc. Perkin. Trans* 1499.

SUMMARY OF THE INVENTION

Pharmaceutical compositions and compounds are provided. The compounds of the invention are substituted pyrazoles and pyrazolines. In one embodiment of the invention, formulations of the compounds in combination with a physiologically acceptable carrier are provided. The pharmaceutical formulations are useful in the treatment of disorders associated with hyperproliferation and tissue remodelling or repair. The compounds are also active in the inhibition of specific protein kinases.

BRIEF DESCRIPTION OF THE DRAWINGS

FIG. 1 is a graph illustrating the anti-tumor activity of KP-15792 in a murine model using Lewis Lung Carcinoma cells.

DETAILED DESCRIPTION OF EMBODIMENTS OF THE INVENTION

The present invention provides novel compounds, compositions and methods as set forth within this specification. In general, all technical and scientific terms used herein have the same meaning as commonly understood to one of ordinary skill in the art to which this invention belongs, unless clearly indicated otherwise. For clarification, listed below are definitions for certain terms used herein to describe the present invention. These definitions apply to the terms as they are used throughout this specification, unless otherwise clearly indicated.

Definition of Terms

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

"Alkyl" is a monovalent, saturated or unsaturated, straight, branched or cyclic, aliphatic (i.e., not aromatic) hydrocarbon group. In various embodiments, the alkyl group has 1–20 carbon atoms, i.e., is a C1–C20 (or $C_1$–$C_{20}$) group, or is a C1–C18 group, a C1–C12 group, a C1–C6 group, or a C1–C4 group. Independently, in various embodiments, the alkyl group: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH=$CH_2$ (ethenyl) and —C≡CH (ethynyl)) and $C_3$alkyl (i.e., —$CH_2CH_2CH_3$ (n-propyl), —CH($CH_3$)$_2$ (i-propyl), —CH=CH—$CH_3$ (1-propenyl), —C≡C—$CH_3$ (1-propynyl), —$CH_2$—CH=$CH_2$ (2-propenyl), —$CH_2$—C≡CH (2-propynyl), —C($CH_3$)=$CH_2$ (1-methylethenyl), and —CH($CH_2$)$_2$ (cyclopropyl)).

"Ar" indicates a carbocyclic aryl group selected from phenyl, substituted phenyl, naphthyl, and substituted naphthyl. Suitable substituents on a phenyl or naphthyl ring include $C_1$–$C_6$alkyl, $C_1$–$C_6$alkoxy, carboxyl, carbonyl ($C_1$–$C_6$)alkoxy, halogen, hydroxyl, nitro, —$SO_3H$, and amino.

"Aryl" is a monovalent, aromatic, hydrocarbon, ring system. The ring system may be monocyclic or fused polycyclic (e.g., bicyclic, tricyclic, etc.). In various embodiments, the monocyclic aryl ring is C5–C10, or C5–C7, or C5–C6, where these carbon numbers refer to the number of carbon atoms that form the ring system. A C6 ring system, i.e., a phenyl ring, is a preferred aryl group. In various embodiments, the polycyclic ring is a bicyclic aryl group, where preferred bicyclic aryl groups are C8–C12, or C9–C10. A naphthyl ring, which has 10 carbon atoms, is a preferred polycyclic aryl group.

"Arylene" is a polyvalent, aromatic hydrocarbon, ring system. The ring system may be monocyclic or fused polycyclic (e.g., bicyclic, tricyclic, etc.). In various embodiments, the monocyclic arylene group is C5–C10, or C5–C7, or C5–C6, where these carbon numbers refer to the number of carbon atoms that form the ring system. A C6 ring system, i.e., a phenylene ring, is a preferred aryl group. In various embodiments, the polycyclic ring is a bicyclic arylene group, where preferred bicyclic arylene groups are C8–C12, or C9–C10. A naphthylene ring, which has 10 carbon atoms, is a preferred polycyclic aryl group. The arylene group may be divalent, i.e., it has two open sites that each bond to another group; or trivalent, i.e., it has three open sites that each bond to another group; or it may have more than three open sites.

"Carbocycle" refers to a ring formed exclusively from carbon, which may be saturated or unsaturated, including aromatic. The ring may be monocyclic (e.g., cyclohexyl, phenyl), bicyclic (e.g., norbornyl), polycyclic (e.g., adamantyl) or contain a fused ring system (e.g., decalinyl, naphthyl). In one embodiment, the ring is monocyclic and formed from 5, 6 or 7 carbons. In one embodiment, the ring is bicyclic and formed from 7, 8 or 9 carbons. In one embodiment, the ring is polycyclic and formed from 9, 10 or 11 carbons. In one embodiment, the ring includes a fused ring system and is formed from 8–12 carbons. Thus, in one embodiment, the carbocycle is formed from 5–12 ring carbons.

"Heteroalkyl" is an alkyl group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted.

"Heteroalkylene" is an alkylene group (as defined herein) wherein at least one of the carbon atoms is replaced with a heteroatom. Preferred heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom, as explained elsewhere herein.

"Heteroaryl" is a monovalent aromatic ring system containing carbon and at least one heteroatom in the ring. The heteroaryl group may, in various embodiments, have one heteroatom, or 1–2 heteroatoms, or 1–3 heteroatoms, or 1–4 heteroatoms in the ring. Heteroaryl rings may be monocyclic or polycyclic, where the polycyclic ring may contained fused, spiro or bridged ring junctions. In one embodiment, the heteroaryl is selected from monocyclic and bicyclic. Monocyclic heteroaryl rings may contain from about 5 to about 10 member atoms (carbon and heteroatoms), preferably from 5–7, and most preferably from 5–6 member atoms in the ring. Bicyclic heteroaryl rings may contain from about 8–12 member atoms, or 9–10 member atoms in the ring. The heteroaryl ring may be unsubstituted or substituted. In one embodiment, the heteroaryl ring is unsubstituted. In another embodiment, the heteroaryl ring is substituted. Exemplary heteroaryl groups include benzofuran, benzothiophene, furan, imidazole, indole, isothiazole, oxazole, piperazine, pyrazine, pyrazole, pyridazine, pyridine, pyrimidine, pyrrole, quinoline, thiazole and thiophene.

"Heteroarylene" is a polyvalent aromatic ring system containing carbon and at least one heteroatom in the ring. In other words, a heteroarylene group is a heteroaryl group that has more than one open site for bonding to other groups. The heteroarylene group may, in various embodiments, have one heteroatom, or 1–2 heteroatoms, or 1–3 heteroatoms, or 1–4 heteroatoms in the ring. Heteroarylene rings may be monocyclic or polycyclic, where the polycyclic ring may contained fused, spiro or bridged ring junctions. In one embodiment, the heteroaryl is selected from monocyclic and bicyclic. Monocyclic heteroarylene rings may contain from about 5 to about 10 member atoms (carbon and heteroatoms), preferably from 5–7, and most preferably from 5–6 member atoms in the ring. Bicyclic heteroarylene rings may contain from about 8–12 member atoms, or 9–10 member atoms in the ring.

"Heteroatom" is a halogen, nitrogen, oxygen, silicon or sulfur atom. Groups containing more than one heteroatom may contain different heteroatoms.

"Heterocycle" refers to a ring containing at least one carbon and at least one heteroatom. The ring may be monocyclic (e.g., morpholinyl, pyridyl), bicyclic (e.g., bicyclo[2.2.2]octyl with a nitrogen at one bridgehead position), polycyclic, or contain a fused ring system. In one embodiment, the ring is monocyclic and formed from 5, 6 or 7 atoms. In one embodiment, the ring is bicyclic and formed from 7, 8 or 9 atoms. In one embodiment, the ring is polycyclic and formed from 9, 10 or 11 atoms. In one embodiment, the ring includes a fused ring system and is formed from 8–12 atoms. Thus, in one embodiment, the heterocycle is formed from 5–12 ring atoms. In one embodiment, the heteroatom is selected from oxygen, nitrogen and sulfur. In one embodiment, the heterocycle contains 1, 2 or 3 heteroatoms.

As used herein, and unless otherwise specified, the terms carbocyclic and heterocyclic encompass both substituted and unsubstituted carbocyclic and heterocyclic groups. In one embodiment, the substitution present on a carbocyclic or heterocyclic group is selected from alkyl, heteroalkyl, aryl, and heteroaryl, preferably alkyl and heteroalkyl. In one embodiment, the alkyl and heteroalkyl substitution present on a carbocyclic or heterocyclic group is selected from $C_1$–$C_6$alkyl, $C_1$–$C_6$alkoxy, halogen, nitro, hydroxyl, cyano, sulfonic acid (i.e., —$SO_3H$), carboxylic acid, carboxylate ester (i.e., —$CO_2R$ where R is, e.g., $C_1$–$C_{10}$alkyl), amino, alkylamino, dialkylamino, acyl (i.e., R—C(=O)—), and acylamino (i.e., R—C(=O)—NH— where R is, e.g., $C_1$–$C_{10}$alkyl). For example, and unless otherwise specified, the terms cyclohexyl and phenyl refer to both substituted and unsubstituted cyclohexyl and phenyl.

"Pharmaceutically acceptable salt" and "salts thereof" in the compounds of the present invention refers to acid addition salts and base addition salts.

Acid addition salts refer to those salts formed from compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts refer to those salts formed from compounds of the present invention and inorganic bases such as sodium, potassium, lithium, ammonium, calcium, magnesium, iron, zinc, copper, manganese, aluminum salts and the like.

Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

Compounds

In one aspect the present invention provides compounds of formula (1), as set forth below.

In another aspect the present invention provides compositions comprising a compound of formula (1)

(1)

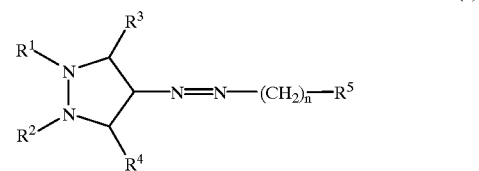

and stereoisomers, solvates, and pharmaceutically acceptable salts thereof, and a pharmaceutically acceptable carrier, diluent or excipient, where $R^1$ and $R^2$ are selected from direct bond, H, and alkyl;

$R^3$ and $R^4$ are selected from —$NH_2$, NHC(=O)$R^5$, and =O;

$R^5$ is selected from $R^6$, $R^7$, and $R^8$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R\ 6)_k$-heteroarylene; $R^8$ is selected from $(R^7)_k$-alkylene, $(R^7)_k$-heteroalkylene, $(R^7)_k$-arylene, and $(R^7)_k$-heteroarylene; and k is selected from 0, 1, 2, 3, 4 and 5; and n is selected from 0, 1, 2, 3, 4 or 5.

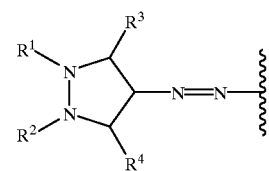

In compounds of formula (1), the structural moiety is used to represent a family of tautomeric structures. In part, the particular tautomeric structure(s) encompassed by formula (1) depend on the selected of $R^3$ and $R^4$. When $R^3$ and $R^4$ are each —$NH_2$, then $R^1$ and $R^2$ are —H and/or direct bonds, as shown in the Scheme below.

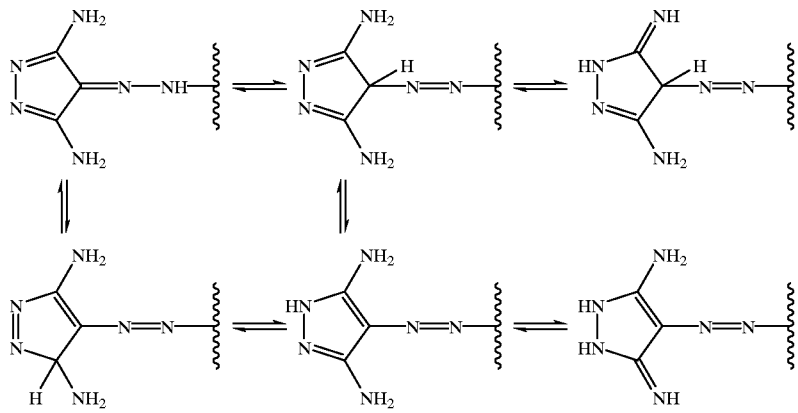

In one embodiment, $R^5$ is selected from carbocyclic and heterocyclic groups, where the carbocyclic and heterocyclic groups preferably contain from 5 to 12 ring atoms. In one embodiment, $R^5$ is a carbocyclic group. In one embodiment, $R^5$ is a heterocyclic group.

In one embodiment, $R^5$ is selected from the carbocyclic groups phenyl and naphthyl. As noted previously, a carbocyclic group may be substituted or unsubstituted. Accordingly, in this embodiment, the phenyl or naphthyl group may be substituted with one or more of, for example, alkyl, alkoxy, hydroxyl, sulfonic acid, carboxylic acid, halogen, amino and acetylamino.

In one embodiment, $R^5$ is selected from a heterocyclic group of the formula

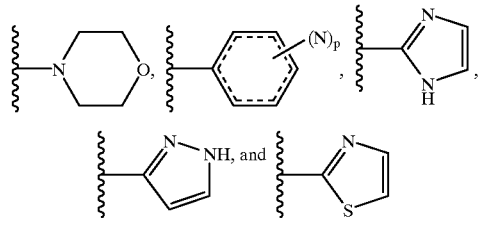

where p is selected from 1, 2 and 3. As used herein, the moiety

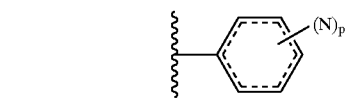

represents a six-membered ring that optionally contains unsaturation and necessarily includes 1, 2 or 3 ring nitrogens. Examples include

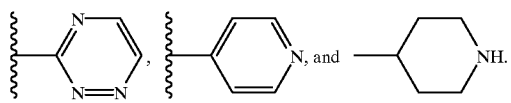

In one embodiment, $R^3$ and $R^4$ are each amino (—$NH_2$) groups. In another embodiment, one of $R^3$ and $R^4$ is an amino group while the other of R and R is a carbonyl (=O) group. In one embodiment, both of $R^3$ and $R^4$ are carbonyl groups. In one embodiment, n is 0. In another embodiment, n is selected from 0, 1 and 2. In another embodiment, n is selected from 1, 2, 3 and 4.

In one embodiment, the compounds and/or compositions and/or methods of the present invention exclude a compound of formula (1) wherein $R^1$=H, and/or $R^2$=H, and/or $R^3$=amino, and/or $R^4$=amino, and/or n=0, and/or $R^5$=4-methoxyphenyl.

Synthetic Methods

Compounds as set forth in compositions and methods of the present invention may be prepared by methods disclosed in the literature, and/or as summarized in Scheme 1.

Scheme 1

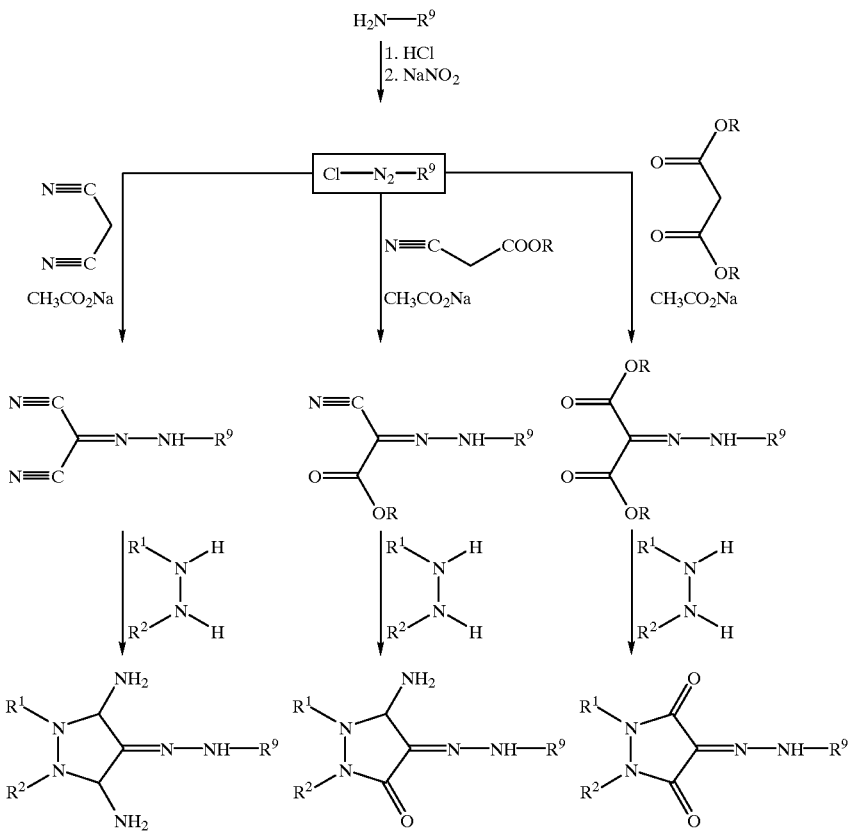

Thus, a primary amine of the formula $H_2N$—$R^9$ (where $R^9$ has been selected to represent —$(CH_2)_n$—$R^5$ of formula (1)) is diazotised by treatment sodium nitrite and hydrochloric acid. The intermediate diazo compound (enclosed by a box in Scheme 1) will, in the presence of base (e.g., sodium acetate as shown in Scheme 1) react with compounds containing an active methylene group, i.e., a compound including a methylene group (—$CH_2$—) flanked by electron withdrawing groups such as cyano (—CN) and/or ester (—COOR), to provide an azo compound. This azo compound may be reacted with a hydrazine derivative to provide compounds of the present invention.

In Scheme 1, $R^1$ and $R^2$ are each preferably hydrogen. However, either or both of $R^1$ and $R^2$ may be an alkyl group.

Pharmaceutical Formulations

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well tolerated by the host. The implant containing the inhibitory compounds is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided inhibitory compounds and other cytotoxic agents has the advantages that the required dosages for the individual drugs is lower, and the effect of the different drugs complementary. Depending on the patient and condition being treated and on the administration route, the subject inhibitory compounds may be administered in dosages of 0.1 μg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with other pharmaceutically active agents, particularly other anti-metastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

Methods of Use

The subject compounds are administered to a subject having a hyperproliferative disorders, e.g. to inhibit tumor growth, to inhibit angiogenesis, to decrease inflammation associated with a lymphoproliferative disorder, to inhibit graft rejection, or neurological damage due to tissue repair, etc. The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g. to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one h and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the cell burden, and may be continued until there are essentially none of the undesirable cells detected in the body.

The compounds also find use in the specific inhibition of signaling pathway mediated by protein kinases. Protein kinases are involved in signaling pathways for such important cellular activities as responses to extracellular signals and cell cycle checkpoints. Inhibition of specific protein kinases provides a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in signaling mediated by protein kinases. Such conditions include those associated with defects in cell cycle regulation or in response to extracellular signals, e.g. hyperglycemia and diabetes Type I and Type II, immunological disorders, e.g. autoimmune and immunodeficiency diseases; hyperproliferative disorders, which may include psoriasis, arthritis, inflammation, angiogenesis, endometriosis, scarring, cancer, etc.

The compounds of the present invention are active in inhibiting purified kinase proteins, i.e. there is a decrease in the phosphorylation of a specific substrate in the presence of the compound. A protein kinase of particular interest in integrin linked kinase (ILK). ILK is a serine threonine kinase. The DNA and predicted amino acid sequence may be accessed at Genbank, no. U40282, or as published in Hannigan et al. (1996) *Nature* 379:91–96. ILK regulates integrin extracellular activity (ECM interactions) from inside the cell via its direct interaction with the integrin subunit. Interfering with ILK activity allows the specific targeting of integrin function, while leaving other essential signaling pathways intact. Increased levels of cellular ILK activity short circuits the normal requirement for adhesion to extracellular membrane in regulating cell growth. Thus, inhibiting ILK activity may inhibit anchorage-independent cell growth.

It is also known that many cell types undergo apoptosis if the appropriate contacts with extracellular matrix proteins are not maintained (anoikis). The induction of apoptosis by the subject compounds in such cells predicts an association with the ILK signaling pathway.

The compounds of the present invention bind to protein kinases at a high affinity, and find use as affinity reagents for the isolation and/or purification of such kinases. Affinity chromatography is used as a method of separating and purifying protein kinases and phosphatases using the biochemical affinity of the enzyme for inhibitors that act on it. The compounds are coupled to a matrix or gel. Preferably a microsphere or matrix is used as the support. Such supports are known in the art and commercially available. The inhibitor coupled support is used to separate an enzyme that binds to the inhibitor from a complex mixture, e.g. a cell lysate, that may optionally be partially purified. The sample mixture is contacted with the inhibitor coupled support under conditions that minimize non-specific binding. Methods known in the art include columns, gels, capillaries, etc. The unbound compounds are washed free of the resin, and the bound proteins are then eluted in a suitable buffer.

The compounds of the invention may also be useful as reagents for studying signal transduction or any of the clinical disorders listed throughout this application.

Hyper-proliferative Disorders of Interest

There are many disorders associated with a dysregulation of cellular proliferation. The conditions of interest include, but are not limited to, the following conditions.

The subject methods are applied to the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g. uterine, testicular and ovarian carcinomas, endometriosis, squamous and glandular epithelial carcinomas of the cervix, etc. are reduced in cell number by administration of the subject compounds Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature. Angiogenesis may be inhibited by affecting the cellular ability to interact with the extracellular environment and to migrate, which is an integrin-specific function, or by regulating apoptosis of the endothelial cells. Integrins function in cell-to-cell and cell-to-extracellular matrix (ECM) adhesive interactions and transduce signals from the ECM to the cell interior and vice versa. Since these properties implicate integrin involvement in cell migration, invasion, intra- and extra-vasation, and platelet interaction, a role for integrins in tumor growth and metastasis is obvious.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1

In Vitro Screen

Compounds were screened using a series of disease related kinase targets, such as integrin linked kinase-1. Synthesized libraries of compounds are tested against each of the targets to find compounds that inhibit one of the targets preferentially. The desired in vitro potency of the inhibitor is such that the compound is useful as a therapeutic agent, i.e. in the nanomolar or micromolar range.

Inhibition of the targets is measured by scintillation counting; the incorporation of radioactive phosphate onto a specific substrate which is immobilized onto a filter paper at the end of the assay. To provide meaningful measurements of inhibition, the assays are performed both in the absence and presence of specific and known inhibitors, and the amount of incorporated radioactivity is compared to provide a baseline measurement.

The baseline activity is the amount of radioactivity incorporated in the absence of inhibitor. The amount of radioactivity incorporated in the presence of an inhibitor is called the 'sample activity', and the % inhibition is expressed by the following formula:

% inhibition=100−(sample activity/baseline activity*100)

and is usually expressed in conjunction with the compound concentration. By using a range of inhibitor concentrations, the $IC_{50}$ of an inhibitor is estimated (i.e. the concentration at which enzymatic activity is reduced by 50%). The $IC_{50}$ of various compounds against a particular target can be compared, where a lower $IC_{50}$ indicates a more potent compound.

Materials and Methods

Inhibition Assay: Compounds listed in Table 1 were lyophilized and stored at −20° C. Stock solutions were made by weighing out the compounds and dissolving them in dimethyl sulfoxide (DMSO) to a standard concentration, usually 20 mM, and stored at −20° C. The compounds were diluted to a starting intermediate concentration of 250 μM in 1% DMSO, then serially diluted across a row of a 96 well plate using serial 2 fold dilution steps. Diluted 100% DMSO was used as a negative control.

5 μl of each compound dilution were robotically pipetted to Costar serocluster plates maintaining the same plate format. All assays consisted of the following volumes:

5 μl diluted compound

10 μl enzyme preparation

5 μl substrate

5 μl assay ATP and were then incubated 15 min at room temperature.

From each reaction, 10 μl of reaction mix was spotted onto Millipore Multiscreen-PH opaque plates and washed 2×10 min in 1% phosphoric acid. The plates were dried for at 40° C. for 30 min, then the substrate phosphate complexes were quantitated by scintillation counting. These Millipore plates are in a 96 well format with immobilized P81 phosphocellulose membranes. Both the phosphorylated and non-phosphorylated form of the substrate bind to the membrane while ATP (unincorporated phosphate) is removed in the subsequent wash steps. Results are shown in Table 1 below.

Integrin Linked Kinase:

The target integrin linked kinase is a full-length recombinant protein expressed in sF9 insect cells by baculovirus infection. The ILK1 substrate is CKRRRLASLR-amide.

Recombinant ILK protein was expressed using cultured insect cells and a baculovirus expression system. Standard techniques for DNA manipulation were used to produce recombinant DNA molecules and baculoviruses (Sambrook. J., Fritsch, E. F. and Maniatis, T. 1989. Molecular cloning, a laboratory manual. Second edition. Cold Spring Harbor Laboratory Press. NY; Crossen, R. and Gruenwald, S. 1998. Baculovirus expression Vector System Manual. $_5$th Edition. Pharmingen, San Diego, Calif.) but the isolation of active ILK required some ingenuity.

The ILK open reading frame (Hannigan et al., supra.), excluding the 5' and 3' untranslated regions, was inserted into the baculovirus transfer vector pAcG2T (Pharmingen) to produce a GST fusion protein under the control of the strong AcNPV polyhedrin promoter. A large scale plasmid preparation of the resulting transfer construct was made using a Qiagen Plasmid Midi Kit. This ILK transfer construct was then co-transfected with BaculoGold DNA (Pharmingen) into Sf9 insect cells (Invitrogen) and a high titre preparation of GST-ILK recombinant baculovirus was produced by amplification in Sf9 cells. Liter scale expression of GST-ILK recombinant protein was done in 1000 ml spinner flasks (Bellco) by infection of Hi5 insect cells (Invitrogen) grown in Ex-Cell 400 Serum Free Media (JRH Biosciences) at a multiplicity of infection of approximately 5. The cells were harvested three days after infection and lysed in Hypotonic Lysis Buffer (HLB; 10 mM imidazole, 5 mM EDTA, 0.1% β-mercaptoethanol, 10 ug/ml PMSF, 1 mM benzamidine) by sonication. The lysate was centrifuged at 10,000 g for 20 min and the supernatant was discarded. The pellet was washed twice in HLB and then washed twice in High Salt Buffer ("HSB"; 500 mM NaCl, 10 mM imidazole, 5 mM EDTA, 0.1% P-mercaptoethanol, 10 ug/ml PMSF, 1 mM benzamidine). The pellet was then resuspended in DNAse-ATP Buffer ("DAB"; 10 mM $MgCl_2$, 1 mM $MnCl_2$, P-methyl aspartic acid, 2 mM NaF, 0.55 mg/ml ATP, 1ug/ml DNAse I, 1% NP-40, 10 mM imidazole, 5 mM EDTA, 0.1% β-mercaptoethanol, 10 ug/ml PMSF, 1 mM benzamidine) and stirred for 30 min at room temperature, and then centrifuged at 10,000×g for 20 min. The pellet was resuspended in High Salt Detergent buffer ("HDB"; 1% NP-40, 1% Triton X-100, 500 mM NaCl, 10 mM imidazole, 5 mM EDTA, 0.1% β-mercaptoethanol, 10 ug/ml PMSF, 1 mM benzamidine), stirred for 30 min at room temperature, and then centrifuged at 10,000 g for 20 min. The pellet was then washed once in each of HDB, HSB, and HLB, centrifuging at 10,000 g each time. Finally, the pellet was resuspended in HLB.

The recombinant ILK expressed in insect cells with a baculovirus system was solubilized by treating the insoluble ILK protein with DNAse I and detergents. This produced an ILK protein preparation in the form of a microparticle suspension. This preparation had a high specific activity and was amenable to automated kinase assays.

TABLE 1

Activity of Analogs of KP-15792

| Codes | Chemical Name | Structure | MW | $IC_{50}$ ($\mu$M) |
|---|---|---|---|---|
| KP-15792 | 3,5-Diamino-4-(p-methoxyphenyl)hydrazono-pyrazole | 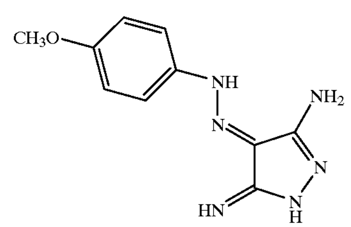 | 232.24 | 1 |
| KP-23194 | 3,5-Diamino-4-phenylhydrazonopyrazole | 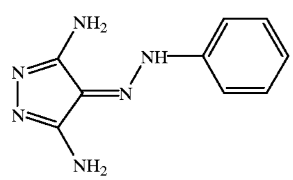 | 202.21 | 0.6 |
| KP-23195 | 3,5-diamino-4-(p-methylphenyl)hydrazonopyrazole | 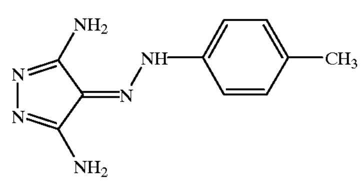 | 216.24 | 5.3 |
| KP-23196 | | 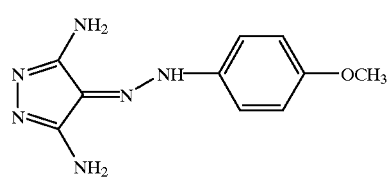 | 234.24 | 0.6 |
| KP-23197 | 3,5-Diamino-4-(3-hydroxy-4-methoxyphenyl)hydrazonopyrazole | 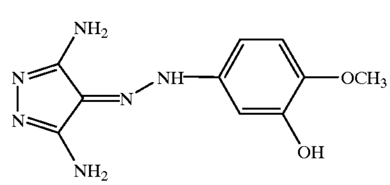 | 248.24 | 4 |

TABLE 1-continued

Activity of Analogs of KP-15792

| Codes | Chemical Name | Structure | MW | IC$_{50}$ ($\mu$M) |
|---|---|---|---|---|
| KP-23198 | 3-Amino-4-phenylazo-2-pyrazolin-5-one | 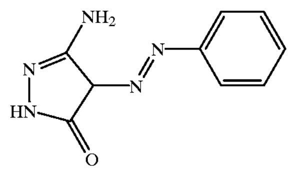 | 203.20 | 17.1 |
| KP-23199 | 3-Amino-4-(p-methylphenylazo)-2-pyrazolin-5-one | 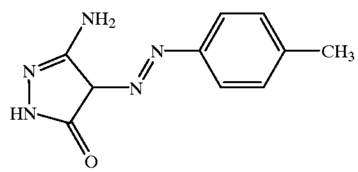 | 217.23 | >20 |
| KP-23200 | 3-Amino-4-(p-methoxyphenylazo)-2-pyrazolin-5-one | 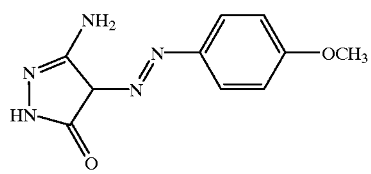 | 233.22 | >20 |
| KP-23201 | 3-Amino-4-(3-hydroxy-4-methyoxyphenylazo)-2-pyrazolin-5-one | 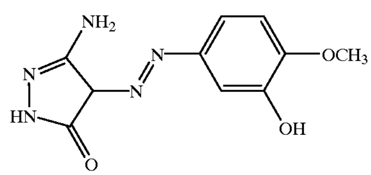 | 249.22 | 18 |
| KP-23202 | 4-Phenylhydrazonopyrazolin-3,5-dione | 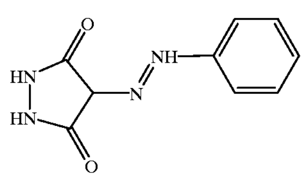 | 204.18 | >20 |
| KP-23203 | 4-(p-Methylphenyl)hydrazonopyrazolin-3,5-dione | 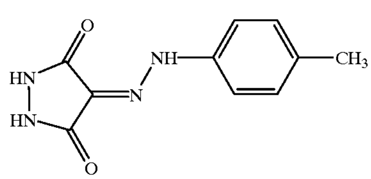 | 218.21 | >20 |
| KP-23204 | 4-(p-Methoxyphenyl)hydrazonopyrazolin-3,5-dione | 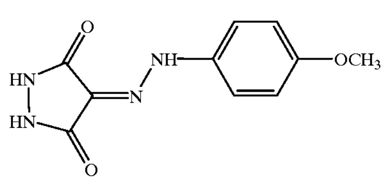 | 234.21 | >20 |
| KP-23205 | 4-(3-hydroxy-4-methyoxyphenyl)hydrazonopyrazolin-3,5-dione | 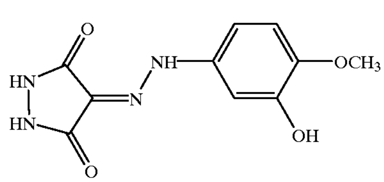 | 250.21 | >20 |

TABLE 1-continued

Activity of Analogs of KP-15792

| Codes | Chemical Name | Structure | MW | IC$_{50}$ ($\mu$M) |
|---|---|---|---|---|
| KP-27288 | 3,5-Diamino-4-(p-sulfonylphenyl)hydrozonopyrazole | 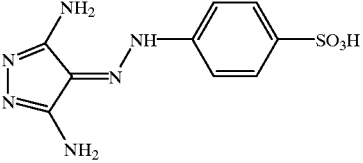 | 282.27 | >20 |
| KP-27289 | 3,5-Diamino-4-morpholinyl-hydrazonopyrazole | 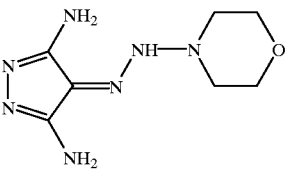 | 211.22 | 9.6 |
| KP-27290 | 3,5-Diamino-4-(2-morpholinylethyl)hydrazonopyrazole | 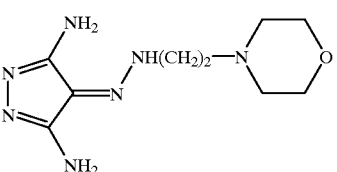 | 239.28 | 8.2 |
| KP-27291 | 3,5-Diamino-4-(2-imidazolyl)hydrazonopyrazole | 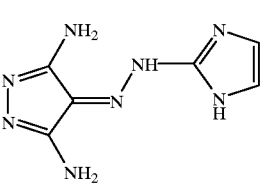 | 192.18 | 28 |
| KP-27292 | 3,5-Diamino-4-(3-pyrazolyl)hydrazonopyrazole | 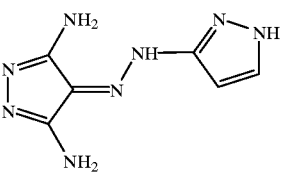 | 192.18 | 8 |
| KP-27293 | 3,5-Diamino-4-(2-thiazolyl)hydrazonopyrazole | 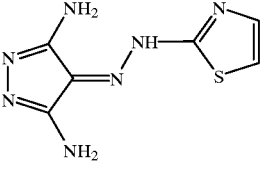 | 209.22 | 0.9 |
| KP-27386 | 3,5-Diamino-4-(4-pipridinylmethyl)hydrazonopyrazole | 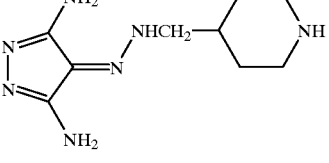 | 223.28 | 13 |
| KP-27387 | 3,5-Diamino-4-(3-[1,2,4]trazinyl)hydrazonopyrazole | 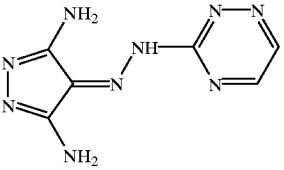 | 205.18 | >20 |

TABLE 1-continued

Activity of Analogs of KP-15792

| Codes | Chemical Name | Structure | MW | IC$_{50}$ ($\mu$M) |
| --- | --- | --- | --- | --- |
| KP-27294 | 3,5-Diamino-4-(1-naphthlyl) hydrazonopyrazole | 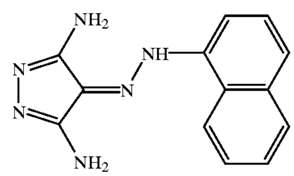 | 252.27 | 0.6 |
| KP-27295 | 4-[N'-(3,5-diaminopyrazol-4-ylidene)hydrazino]naphthalene-1-sulphonic acid | 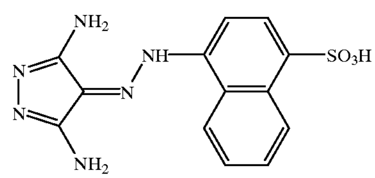 | 332.33 | 19.3 |
| KP-27388 | 4-[N'-(3,5-diaminopyrazol-4-ylidene)hydrazino]benzoic acid | 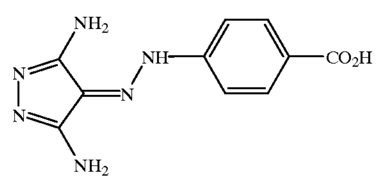 | 246.22 | 13 |
| KP-27389 | 3,5-Diamino-4-(p-hydroxyphenyl) hydrazonopyrazole | 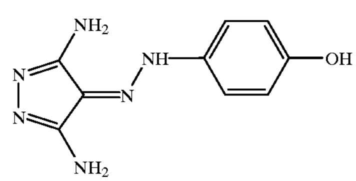 | 218.21 | >20 |
| KP-27390 | 3,5-Diamino-4-(p-chlorophenyl) hydrazonopyrazole | 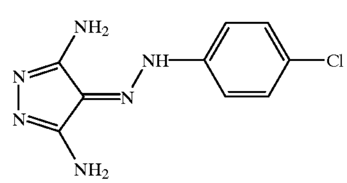 | 236.66 | 1.2 |
| KP-27391 | 3,5-Diamino-4-(p-(n-propyl)phenyl) hydrazonopyrazole | 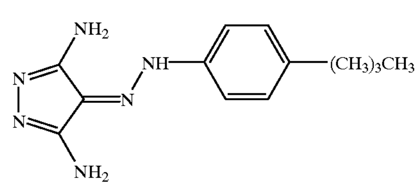 | 258.32 | 4.6 |
| KP-27392 | 3,5-Diamino-4-(p-acetoaminophenyl) hydrazonopyrazole | 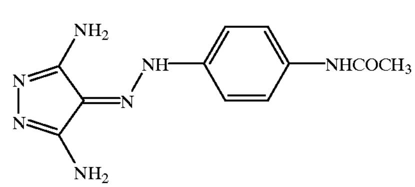 | 274.3 | 5 |

TABLE 1-continued

Activity of Analogs of KP-15792

| Codes | Chemical Name | Structure | MW | IC$_{50}$ ($\mu$M) |
|---|---|---|---|---|
| KP-27393 | 3,5-Diamino-4-(2-hydroxynaphthyl) hydrazonopyrazole | 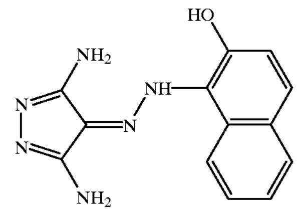 | 268.27 | 3 |

Example 2

Inhibition of Angiogenesis

The test compounds were tested in several angiogenesis related assays. Angiogenesis is an important component of tumour growth and inflammation, and for this reason was deemed a descriptive model. Endothelial proliferation, thymidine incorporation proliferation, invasion and chick chorioallantoic membrane were models used.

Materials and Methods

Endothelial cell cultures:

Cell lines used include HUVEC, EJG and MS1 and are routinely passaged 1 to 2 times weekly. Endothelial growth media (EGM) consists of Endothelial Base Media plus all supplements (Clonetics). For testing of compounds, endothelial cells were plated on 1% gelatin-coated plates. Prior to plating, gelatin solution was added to the plates for at least 10 minutes before plating, but excess solution removed immediately before adding cells. Sterile gelatin solution consists of 1% gelatin in dH$_2$0 that has been autoclaved. Endothelial cells form a characteristic cobblestone monolayer upon confluency. Typically, a T-75 plate contains 1 million microvascular cells upon confluency.

a. Proliferation in Response to Test compounds:

HUVEC endothelial cells were cultured in 96-well plates and treated with a dilution series of test compounds for potential angiogenesis-related effects.

Day 0—Endothelium are plated at 10,000 cells/well.

Day 1—Treatments are added in EGM culture medium in an appropriate dilution series (n=6 or 12). Controls included EGM alone, serum free medium (SFM), and EGM plus 0.5%DMSO.

Day 1–2, MTS/PMS solutions were added and plates read at 4 and 24 h after treatment.

Result: KP-15792 inhibited HUVEC proliferation. See Table 2 below.

b. Thymidine incorporation proliferation assay:

This assay measures cell proliferation by examining the incorporation of radiolabeled nucleotides (3H-thymidine) into newly formed DNA 24 h after addition of the compound. DNA replication is a well accepted measure of cell proliferation.

Materials and Methods:

Cells were plated out and grown overnight. The next day the test compound or controls were added to the plates, along with diluted $^3$H-thymidine added to a final concentration of 0.1 $\mu$Ci/well, and the plates were incubated. After 24 h, the plates were spun down 1000 g for 10 min (for non-adherent cells) before removing the PBS. 120 $\mu$l of the scintillant fluid was added to each of the wells, and the plate was read.

Results:

Test compound inhibited $^3$H-Thymidine incorporation.

c. Migration Assay:

Migration was studied using a simple streak assay. Approximately 2×1 PC3 (a prostate cancer cell line) cells were added to a 6 well plate in 2 ml media plus serum and cells were grown to confluence. A cell scraper was used to remove a strip of cells from the middle of the well, and media with floating cells was also removed. The edge was permanently marked under a phase microscope. The wells were washed with phosphate buffered saline ("PBS") to remove the remaining floating cells and then 5 ml of fresh media plus serum containing 50 $\mu$M of the test compound in DMSO was added, one concentration to each consecutive well. To the control well, DMSO alone in the same volume was added. The plate was incubated at 37° Celsius for 3 to 4 days, and then examined for newly grown cells in the margin.

TABLE 2

| Compound | Inhibition of Migration In PC3 |
|---|---|
| KP-15792 | +++ |
| KP-23200 | ++ |
| KP-23203 | + |
| KP-15760 | ++ |
| KP-15768 | +++ |
| KP-27290 | + |
| KP-27293 | + |
| KP-27294 | + | d. Invasion Assays:

Invasion of cells into surrounding tissue is a hallmark property of tissue remodeling. Tissue remodeling occurs during most pathological progression, including tumor progression, angiogenesis and during normal processes such as wound healing. The following invasion assays were performed using Biocoat® Cell Environments™ Matrigel Invasion Chamber 24-Well Plate Size (Becton Dickinson). The invasion chambers can be used to assess the ability of a cell to traverse an extracellular matrix under a variety of conditions. The chambers consist of a 24 well plate and 12 inserts that can be suspended in each well and act as an upper chamber. Cells place in the upper chamber insert must invade through a matrix in order to enter the lower chamber.

The intestinal epithelial cell line, IEC-18, which naturally expressed ILK, was shown to be invasive in is assay. Invasion data for ILK inhibitors administered to both the parental IEC-18 and the IEC-18-13 cells engineered to over-express ILK (Cell line a gift from Dr. Shoukat Dedhar, BC Cancer Research Centre, Vancouver, BC).

Cells were pre-labeled with $^3$H-thymidine overnight. Typically, 5×10$^5$ cells are cultured overnight in 5 mls of serum-containing media spiked with 200 μl of thymidine stock solution. Cells were scraped off of the flask substratum and gently pipetted up and down to achieve single cell suspension in the medium. Cell numbers were estimated using a hemocytometer.

Approximately 2×10$^5$ cells were added to a 6 well plate in 1 ml serum-containing media and then allowed to attach and invade through a matrix towards a chemoattractant in the lower chamber overnight. The bottom chamber or well of the 24 well plate contained with 1 ml of serum containing media and either 10 ng/ml of vitronectin or fibronectin as chemoattractant.

After an incubation period of 24 h, media was carefully removed from the upper chamber insert and saved for scintillation counting. Cells that did not invade were removed from the upper surface of the filter using a cotton swab. The filters containing cells that had invaded the matrix were removed carefully from the chamber insert with a scalpel and placed in scintillation vials. The media was also collected from the lower chamber and placed in a scintillation vial. The relative amount of cell invasion was calculated by adding counts from the filters and lower chambers and dividing this sum by the total counts added initially to the upper chambers. The percentage of total counts that invaded was compared between drug-treated and untreated groups.

Results:

The therapeutic compound KP-15792 was shown to be efficacious in inhibiting cellular invasion in this model to 46.9% of the control (data not shown).

e. Chick chorioallantoic membrane assay ("CAM" assay): was performed on fertilized chicken eggs and used as a test for angiogenesis inhibition.

Approximately 4 dozen fertilized eggs were sprayed with 70% ETOH and placed in a 180 egg incubator (GQF Sportsman incubator). The eggs were incubated "rounded-side down" and were rotated 360 degrees along the vertical axis every 30 minutes at 37° C. under 90% relative humidity.

After 4 days, the eggs were placed upside down (round side up) for 5–10 minutes, before a round hole approximately 3 centimeters in diameter was created above the pointed end or "air hole" of the egg using sterile blunt-ended forceps ("deshelling"). The inner membrane was also removed, and the embryo was visible through this opening. A small portion of the outer membrane was then carefully removed using fine-tipped forceps in order to expose the CAM. Sterile Parafilm™ was placed over the de-shelled opening to create an airtight seal. The eggs are returned to the incubator (with no rotation) for 2 days.

Viable eggs were then treated with control and inhibitor compounds (50 μM). Gelfoam™ gelatin sterile sponge (Upjohn) or 1–2 mm discs of methlycellulose saturated with physiological saline, buffer or an appropriate dilution of the compounds under investigation. The Gelfoam™ fragments of methylcellulose discs were added directly to the surface of the developing CAM. Care was taken not to add the treatment directly over a large vessel. The shells were marked in 3 places to aid in stereotactic localization of the treatment sponge or disc. An average of 6 eggs were used for each experimental condition. The treated eggs were returned to the incubator for 2 days.

Then, CAMs were assessed visually for blood vessel growth inhibition. Photomicrographs for records and visual examination were made using a Nikon dissecting microscope with an attatched Nikon 35-mm camera body.

Results:

TABLE 3

Data from CAM Developmental Angiogenesis Assay

| Compound | Number of assays | Inhibition of Angiogenesis |
|---|---|---|
| KP-15792 | 41 | 34% |
| KP-23200 | 3 | 66% |
| KP-23203 | 5 | 80% |
| KP-15760 | 14 | 78% |
| KP-15768 | 14 | 50% |
| KP-27290 | 9 | 44% |
| KP-27293 | 11 | 54% |
| KP-27294 | 10 | 80% |

Example 3

Assessment of Effects on Cell Viability

Anti-tumour efficacy and dose response in allograft and xenograft models. Cell lines were selected from an in vitro assay based on ILK expression, and growth curves characterized in vivo. Preliminary tests were performed with the Lewis Lung cell line in a murine allograft tumor model. In parallel, human xenograft tumor lines were characterized.

Cells were inoculated subcutaneously in the rear flank of mice, and the test compound was administered i.p. daily. Tumors were measured and the size calculated, with the objective being a decrease in tumor growth compared to the controls.

The results demonstrated that KP-15792 succeeded in reducing tumor growth and the results are shown in FIG. 1.

Example 4

Synthesis of 3,5-Diamino-4-(p-methoxyphenyl) hydrazonopyrazole

Unless otherwise stated, chemical reactants and reagents were obtained from standard chemical supply houses, such as Aldrich (Milwaukee, Wis.; www.aldrich.sial.com); and Lancaster Synthesis, Inc. (Windham, N.H.; www.lancaster.co.uk).

To a flask containing p-anisidine (5.46 g, 44.3 mmol) and concentrated HCl solution (11 mL) in 75 mL of water, cooled in an ice water bath, was added sodium nitrite solution (4.57 g, 66.3 mmol). The resulting mixture was then added to a solution of malononitrile (4.79 g, 72.6 mmol) in a mixture of MeOH (12 mL) and water (25 mL). A large quantity of yellow solid quickly precipitated. The mixture was stirred for about 30 minutes at room temperature. The solid was collected and purified by recrystallization in hot EtOH. The product (6.17 g, 70%) was obtained as a yellow solid.

To a suspension of the yellow solid (2.00 g) prepared above in 10 mL of EtOH was added hydrazine hydrate (2.0 mL). This mixture was refluxed for about 3 h. The yellow solid was collected and purified by recrystallization in hot EtOH. The product was isolated as yellow cotton like solid (1.50 g, 65%).

m.p.: 263–265° C.

$^1$H NMR (ppm, in DMSO-d$_6$): 10.73 (s, br, 1 H), 7.69 (m, 2 H), 6.99 (m, 2 H), 6.00 (s, br, 4 H), 3.81 (s, 3 H).

$^{13}$C NMR (ppm, in DMSO-d$_6$): 158.4, 147.6, 121.7, 114.0, 113.4, 99.9, 55.3.

FTIR (cm$^{-1}$, KBr pellet): 3401, 3301, 3187, 1603, 562, 1498, 1248, 1033, 828.

Mass spectrometry (m/e, EI): 232 (M+, 100%).

Elemental analysis for $C_{10}H_{12}N_6O$ (obtained/calcd.): C 52.28/51.72, H 5.18/5.21, N 35.88/36.19.

Example 5

Additional Syntheses According To Procedure of Example 4

The following compounds were synthesized using malononitrile, following essentially the same procedure as described above in Example 4:
3,5-Diamino-4-phenylhydrazonopyrazole;
3,5-diamino-4-(p-methylphenyl)hydrazonopyrazole;
3,5-Diamino-4-(3-hydroxy-4-methoxyphenyl)hydrazonopyrazole;
4-[N'-(3,5-diaminopyrazole-4-ylidene)hydrazino]benzene sulfonic acid;
3,5-Diamino-4-morpholinylhydrazonopyrazole;
3,5-Diamino-4-(2-morpholinylethyl)hydrazonopyrazole;
3,5-Diamino-4-(2-imidazolyl)hydrazonopyrazole;
3,5-Diamino-4-(3-pyrazolyl)hydrazonopyrazole;
3,5-Diamino-4-(2-thiazolyl)hydrazonopyrazole;
3,5-Diamino-4-(1-naphthalyl)hydrazonopyrazole;
4-[N'-(3,5-diaminopyrazole-4-ylidene)hydrazino]napthalene-1-sulfonic acid;
3,5-Diamino-4-(4-piperidinylmethyl)hydrazonopyrazole;
3,5-Diamino-4-(3-[1,2,4]trazinyl)hydrazonopyrazole;
4-[N'-(3,5-diaminopyrazole-4-ylidene)hydrazino]benzene acid
3,5-Diamino-4-(p-hydroxyphenyl)hydrazonopyrazole;
3,5-Diamino-4-(p-chlorophenyl)hydrazonopyrazole;
3,5-Diamino-4-(p-(n-propyl)phenyl)hydrazonopyrazole;
3,5-Diamino-4-(p-acetoaminophenyl)hydrazonopyrazole; and
3,5-Diamino-4-(2-hydroxynaphthanyl)hydrazonopyrazole.

Example 6

Additional Syntheses According To Procedure of Example 4, using Ethyl Cyanoacetate The following compounds were synthesized using ethyl cyanoacetate instead of malononitrile, but otherwise following essentially the same procedure as described above in Example 4:
3-Amino-4-phenylazo-2-pyrazolin-5-one;
3-Amino-4-(p-methylphenylazo)-2-pyrazolin-5-one;
3-Amino-4-(p-methoxyphenylazo)-2-pyrazolin-5-one; and
3-Amino-4-(3-hydroxy-4-methyoxyphenylazo)-2-pyrazolin-5-one.

Example 7

Additional Syntheses According To Procedure of Example 4, using Diethyl Malonate The following compounds were synthesized using diethyl malonate instead of malononitrile, but otherwise following essentially the same procedure as described above in Example 4:
4-Phenylhydrazonopyrazolin-3,5-dione;
4-(p-Methylphenyl)hydrazonopyrazolin-3,5-dione;
4-(p-Methoxyphenyl)hydrazonopyrazolin-3,5-dione; and
4-(3-hydroxy-4-methyoxyphenyl)hydrazonopyrazol in-3,5-dione.

From the foregoing it will be appreciated that, although specific embodiments of the invention have been described herein for purposes of illustration, various modifications may be made without deviating from the spirit and scope of the invention. Accordingly, the invention is not limited except as by the appended claims.

All publications mentioned herein are incorporated herein by reference for the purpose of describing and disclosing. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A composition comprising a compound of formula (1)

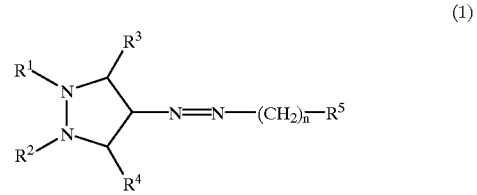

or a stereoisomer, solvate, or a pharmaceutically acceptable salt thereof, and a pharmaceutically acceptable carrier, diluent or excipient, where $R^1$ and $R^2$ are selected from H and direct bond;

$R^3$ and $R^4$ are selected from —$NH_2$, NHC(=O)$R^5$, and =O;

$R^5$ is selected from $R^6$, $R^7$, and $R^8$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R^6)_k$-heteroarylene; $R^8$ is selected from $(R^7)_k$-alkylene, $(R^7)_k$-heteroalkylene, $(R^7)_k$-arylene, and $(R^7)_k$-heteroarylene; and k is selected from 0, 1, 2, 3, 4 and 5; and n is selected from 0, 1, 2, 3, 4 or 5.

2. The composition of claim 1 wherein $R^3$ and $R^4$ are each —$NH_2$ or NHC(=O)$R^5$.

3. The composition of claim 2 wherein $R^3$ and $R^4$ are each —$NH_2$.

4. The composition of claim 1 wherein at least one of $R^3$ and $R^4$ is =O.

5. The composition of claim 1 wherein $R^5$ is selected from carbocyclic and heterocyclic groups.

6. The composition of claim 5 wherein the carbocyclic and heterocyclic groups contain 5–12 ring atoms.

7. The composition of claim 1 wherein $R^5$ is a carbocyclic group selected from monocyclic and fused ring groups.

8. The composition of claim 1 wherein $R^5$ is a heterocyclic group containing from 1–3 nitrogens.

9. The composition of claim 1 wherein $R^5$ is selected from $R^6$ and $R^7$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R^6)_k$-heteroarylene; and k is selected from 0, 1, 2, 3, 4 and 5.

10. The composition of claim 1 wherein the compound of formula (1) is selected from 3,5-Diamino-4-(p-methoxyphenyi)hydrazonopyrazole;

3,5-Diamino-4-phenylhydrazonopyrazole;

3,5-diamino-4-(p-methylphenyl)hydrazonopyrazole;

3,5-Diamino-4-(3-hydroxy-4-methoxyphenyl)hydrazonopyrazole;

4-[N'-(3,5-diaminopyrazole-4-ylidene)hydrazino]benzenesulfonic acid;

3,5-Diamino-4-morpholinylhydrazonopyrazole;

3,5-Diamino-4-(2-morpholinylethyl)hydrazonopyrazole;
3,5-Diamino-4-(2-imidazolyl)hydrazonopyrazole;
3,5-Diamino-4-(3-pyrazolyl)hydrazonopyrazole;
3,5-Diamino-4-(2-thiazolyl)hydrazonopyrazole:
3,5-Diamino-4-(1-naphthyl)hydrazonopyrazole;
4-[N'-(3,5diaminopyrazole-4-ylidene)hydrazino] naphthalene-1-sulfonic acid;
3,5-Diamino-4-(4-piperidinylmethyl)hydrazonopyrazole;
3,5-Diamino-4-(3-[1,2,4]-triazinyl)hydrazonopyrazole;
4-[N'-(3,5-diaminopyrazol-4-ylidene)hydrazino]benzoic acid;
3,5-Diamino-4-(p-hydroxyphenyl)hydrazonopyrazole;
3,5-Diamino-4-(p-chlorophenyl)hydrazonopyrazole;
3,5-Diamino-4-(p-(n-propyl)phenyl)hydrazonopyrazole;
3,5-Diamino-4-(p-acetoaminophenyl) hydrazonopyrazole; and
3,5-Diamino-4-(1-(2-hydroxynaphthyl) hydrazonopyrazole.

11. The composition of claim 1 wherein the compound of formula (1) is selected from
3-Amino-4-phenylazo-2-pyrazolin-5-one;
3-Amino-4-(p-methylphenylazo)-2-pyrazolin-5-one;
3-Amino-4-(p-methoxyphenylazo)-2-pyrazolin-5-one; and
3-Amino-4-(3-hydroxy-4-methoxyphenylazo) 2-pyrazolin-5-one.

12. The composition of claim 1 wherein the compound of formula (1) is selected from
4-Phenylhydrazonopyrazolin-3,5-dione;
4-(p-Methylphenyl)hydrazonopyrazolin-3,5-dione;
4-(p-Methoxyphenyl)hydrazonopyrazolin-3,5-dione; and
4-(3-hydroxoy-4-methoxyphenyl)hydrazonopyrazolin-3,5-dione.

13. A method of treating a hyperproliferative disorder, the method comprising:
contacting a patient suffering from said hyperproliferative disorder with an effective dose of a compound of the formula:

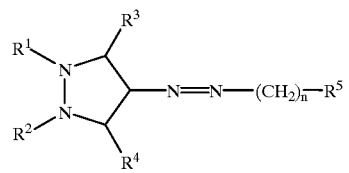

(1)

or a stereoisomer, solvate, or a pharmaceutically acceptable salt thereof, and a pharmaceutically acceptable carrier, diluent or excipient, where $R^1$ and $R^2$ are selected from H and direct bond;

$R^3$ and $R^4$ are selected from —$NH_2$, $NHC(=O)R^5$, and =O;

$R^5$ is selected from $R^6$, $R^7$, and $R^8$, where $R^6$ is selected from alkyl, heteroalkyl, aryl and heteroaryl; $R^7$ is selected from $(R^6)_k$-alkylene, $(R^6)_k$-heteroalkylene, $(R^6)_k$-arylene and $(R^6)_k$-heteroarylene; $R^8$ is selected from $(R^7)_k$-alkylene, $(R^7)_k$-heteroalkylene, $(R^7)_k$-arylene, and $(R^7)_k$-heteroarylene; and k is selected from 0, 1, 2, 3, 4 and 5; and n is selected from 0, 1, 2, 3, 4 or 5.

14. The method of claim 13, wherein said hyperproliferative disorder comprises the growth of solid tumor carcinoma cells.

15. The method of claim 13, wherein said hyperproliferative disorder comprises angiogenesis.

16. The method of claim 13, wherein said hyperproliferative disorder comprises neointimal hyperplasia.

17. The method of claim 13, wherein said hyperproliferative disorder is a lymphoproliferative disorder.

18. The method of claim 13, wherein said compound inhibits cellular migration.

* * * * *